US012577212B2

(12) United States Patent
García et al.

(10) Patent No.: US 12,577,212 B2
(45) Date of Patent: Mar. 17, 2026

(54) COMPOUND AND AN ORGANIC SEMICONDUCTING LAYER, AN ORGANIC ELECTRONIC DEVICE AND A DISPLAY OR LIGHTING DEVICE COMPRISING THE SAME

(71) Applicant: Novaled GmbH, Dresden (DE)

(72) Inventors: Elena Galán García, Dresden (DE); Lidia Marin, Dresden (DE); Bodo Wallikewitz, Dresden (DE)

(73) Assignee: Novaled GmbH, Dresden (DE)

( * ) Notice: Subject to any disclaimer, the term of this patent is extended or adjusted under 35 U.S.C. 154(b) by 907 days.

(21) Appl. No.: 17/428,782

(22) PCT Filed: Feb. 5, 2020

(86) PCT No.: PCT/EP2020/052844

§ 371 (c)(1),
(2) Date: Aug. 5, 2021

(87) PCT Pub. No.: WO2020/161179

PCT Pub. Date: Aug. 13, 2020

(65) Prior Publication Data

US 2022/0002218 A1 Jan. 6, 2022

(30) Foreign Application Priority Data

Feb. 6, 2019 (EP) .................................... 19155729

(51) Int. Cl.
*C07D 241/12* (2006.01)
*C07C 13/66* (2006.01)
(Continued)

(52) U.S. Cl.
CPC ............ *C07D 241/12* (2013.01); *C07C 13/66* (2013.01); *H10K 50/16* (2023.02); *H10K 85/622* (2023.02);
(Continued)

(58) Field of Classification Search
None
See application file for complete search history.

(56) References Cited

U.S. PATENT DOCUMENTS 8,568,902 B2 10/2013 Kubota et al.
2002/0121860 A1* 9/2002 Seo .............................. 313/506
(Continued)

FOREIGN PATENT DOCUMENTS

CN 107778260 3/2018
CN 108431980 A 8/2018
(Continued)

OTHER PUBLICATIONS

Machine translated English version of JP 2005/243266 A and the original JP 2005/243266 A, Masayoshi Yabe (Year: 2005).*
(Continued)

*Primary Examiner* — Seokmin Jeon
(74) *Attorney, Agent, or Firm* — Eversheds Sutherland (US) LLP

(57) ABSTRACT

The present invention relates to a compound of Formula (I): an organic semiconducting layer comprising the same, an organic electronic device comprising the organic semiconducting layer and a display device or a lighting device comprising the organic electronic device.

(I)

(Continued)

10 Claims, 2 Drawing Sheets

(51) Int. Cl.

| | |
|---|---|
| ***H10K 50/11*** | (2023.01) |
| ***H10K 50/16*** | (2023.01) |
| ***H10K 50/18*** | (2023.01) |
| ***H10K 85/60*** | (2023.01) |
| ***H10K 101/30*** | (2023.01) |

(52) U.S. Cl.
CPC .......... *H10K 85/654* (2023.02); *H10K 50/11* (2023.02); *H10K 50/18* (2023.02); *H10K 2101/30* (2023.02)

(56) References Cited

U.S. PATENT DOCUMENTS

| | | | | |
|---|---|---|---|---|
| 2007/0055085 | A1* | 3/2007 | Kubota | 585/26 |
| 2012/0001161 | A1* | 1/2012 | Nakano | 257/40 |
| 2016/0301010 | A1 | 10/2016 | Park | |
| 2017/0222152 | A1* | 8/2017 | Haketa | H01L 51/0054 |
| 2019/0263735 | A1 | 8/2019 | Low et al. | |

FOREIGN PATENT DOCUMENTS

| | | | |
|---|---|---|---|
| CN | 108707136 | A | 10/2018 |
| EP | 3312899 | A1 | 4/2018 |
| EP | 3150579 | | 2/2021 |
| KR | 20160095667 | A | 8/2016 |
| KR | 20170086211 | A | 7/2017 |

OTHER PUBLICATIONS

Shiv Kumar et al. "High Tg fluoranthene-based electron transport materials for organic light-emitting diodes", New J. Chem. 2015, vol. 39, p. 6351-6357 (Year: 2015).*

Communication Pursuant to Article 94(3) EPC, European Patent Application No. 19 155 729.7, mailed Jun. 21, 2022.

Notification of First Office Action issued in China application No. 202080019063.5, dated Jul. 5, 2023, 26 pages.

PCT International Search Report and Written Opinion for PCT Application No. PCT/EP2020/052844 mailed Mar. 30, 2020 (11 pages).

Notice to File a Response issued in application No. 10-2021-7028372, dated Dec. 12, 2024 (14 pages).

* cited by examiner

COMPOUND AND AN ORGANIC SEMICONDUCTING LAYER, AN ORGANIC ELECTRONIC DEVICE AND A DISPLAY OR LIGHTING DEVICE COMPRISING THE SAME

CROSS REFERENCE TO RELATED APPLICATIONS

This application is a U.S. national phase application of PCT/EP2020/052844, filed Feb. 5, 2020, which claims priority to European Application No. 19155729.7, filed Feb. 6, 2019. The content of these applications is incorporated herein by reference.

The present invention relates to a compound as well as to an organic semiconducting layer comprising the same. The invention farther relates to an organic electronic device comprising the organic semiconducting layer, respectively the compound. Furthermore, the invention is related to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical PLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

A variety of aryl- and heteroaryl-containing compounds is known in the art for use in organic electronic applications, especially in electron transport materials of organic electronic devices.

However, there is still a need to improve the electronic properties of respective compounds for use in organic electronic devices, in particular to provide compounds having a LUMO farther away from vacuum level, a higher dipole moment, improved melting point and suitable rate onset temperature compared to compounds known in the art. Furthermore, there is still a need to provide compounds suitable to improve the performance of organic electronic devices, in particular to improve the stability (life time) thereof.

It is therefore an object of the present invention to provide novel organic electronic devices and compounds for use therein overcoming drawbacks of the prior art, in particular to provide novel compounds having improved properties, in particular melting points and/or glass transition temperatures and/or electronic properties and/or rate onset temperature which may be suitable to improve the performance and/or life time of organic electronic devices, in particular when used in an electron transport layer thereof.

SUMMARY OF THE INVENTION

The above object is achieved by a compound of Formula (I)

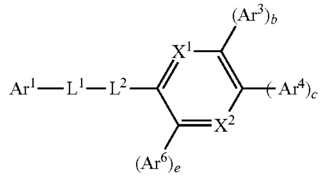

wherein $Ar^1$ is a substituted or unsubstituted $C_{1-6}$ to $C_{36}$ condensed aryl group comprising at least four fused rings and at least two of the fused rings share at least two carbon atoms with each other, wherein the one or more substituent(s), if present in $Ar^1$, are independently selected from the group consisting of $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, $PY(R)_a$, OR, SR, (C═O)R, (C═O)$N(R)_2$, $Si(R)_3$, (S═O)R, and $(S═O)_2R$, Wherein, Y is O or S, R are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

$X^1$ and $X^2$ are nitrogen, or $X^1$ is C—$(Ar^2)_a$ and $X^2$ is C—$(Ar^5)_d$;

$L^1$ may represent a single bond or is a $C_6$ to $C_{24}$ arylene group;

$L^2$ is a substituted or unsubstituted $C_6$ to $C_{30}$ arylene group, substituted or unsubstituted $C_3$ to $C_{25}$ heteroarylene group, wherein the one or more substituent (s), if present in $L^2$, are independently selected from the group consisting of $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, $PY(R)_2$ with Y being O or S, OR, SR, (C═O)R, (C═O)$N(R)_2$, $Si(R)_3$, (S═O)R, and $(S═O)_2R$, wherein, Y is O or S, R are independently selected from $C_1$-$C_{20}$ linear alkyl, $C_1$-$C_{20}$ alkoxy-, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

$Ar^2$, $Ar^3$, $Ar^4$, $Ar^5$ and $Ar^6$ are independently selected from the group consisting of substituted or unsubstituted $C_6$ to $C_{30}$ aryl, substituted or unsubstituted $C_2$ to $C_{30}$ heteroaryl, wherein the one or more substituent(s), if present in $Ar^2$, $Ar^3$, $Ar^4$, $Ar^5$ and $Ar^6$, are independently selected from the group consisting of D, F, CN, $C_4$ to $C_{18}$ alkyl, $C_1$ to $C_{16}$ alkoxy, nitrile, and $PY(R)_2$, OR, SR, (C═O)R, (C═O)$N(R)_2$, $Si(R)_3$, (S═O)R, and $(S═O)_2R$, wherein Y is O or S, R are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{30}$ branched alkoxy, $C_3$-$C_{20}$ cyclic alkoxy, $C_3$-$C_{20}$ branched thioalkyl, $C_3$-$C_{20}$ cyclic thioalkyl, $C_3$-$C_{20}$ aryl and $C_3$-$C_{20}$ heteroaryl;

a, b, c, d and e are independently selected from 0 or 1, wherein $2 \leq a+b+c+d+e \leq 5$; and provided that if for $X^1$ is C—$(Ar^2)_a$ and $X^2$ is C—$(Ar^5)_d$, and b and d are 1 and a+b+c+d+e=2, then $Ar^2$, $Ar^3$, $Ar^4$, $Ar^5$ and $Ar^6$ are independently selected from the group consisting of substituted or unsubstituted $C_6$ to $C_{30}$ aryl.

It was surprisingly found by the inventors that the compound of Formula (I) solves the problem underlying the invention, in particular with respect to the life time of an organic electronic device comprising the same. Life time (LT97, 30 mA/$cm^2$) of an organic electronic device is one of the ley parameter, which defines its overall performance. Organic matrix compounds which provide organic electronic devices with long Me time (LT97, 30 mA/$cm^2$) are highly desired. The compound of formula 1 provides an organic electronic device with improved life time (LT97, 30 mA/$cm^2$) with a comparable performance parameters e.g. voltage and efficiency.

According to another aspect of the present invention if one or more of $Ar^1$, $Ar^2$, $Ar^3$, $Ar^4$, $Ar^5$, $Ar^6$, $R^1$, $L^1$, $L^2$ and substituent(s) on one or more of $Ar^1$, $Ar^2$, $Ar^3$, $Ar^4$, $Ar^5$, $Ar^6$, $L^1$ and $L^2$ is a carbon containing group comprising at least one carbon atom directly connected with at least one hydrogen atom, the hydrogen atoms comprised in the carbon-containing group may be partially or fully replaced by deuterium atoms and/or fluorine atoms.

According to another aspect of the present invention $L^1$ represents a single bond in compound of Formula (I).

According to another aspect of the present invention $L^2$ in the compound of Formula (I) is a substituted or unsubstituted $C_6$ to $C_{30}$ arylene group.

According to another aspect of the present invention $L^2$ in the compound of Formula (I) is $C_3$ to $C_{25}$ heteroarylene group.

The compound of Formula (I) may have the following Formula (II)

(II)

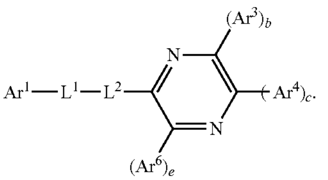

According to another aspect of the present invention $L^1$ represents a single bond in compound of Formula (II).

According to another aspect of the present invention $L^2$ in the compound of Formula (II) is a substituted or unsubstituted $C_6$ to $C_{30}$ arylene group.

According to another aspect of the present invention $L^2$ in the compound of Formula (II) is $C_3$ to $C_{25}$ heteroarylene group.

In this way, it is possible to further improve the relevant properties of the compound of Formula (I) regarding LUMO, dipole moment, melting point and rate onset temperature and to further improve the performance of the organic electronic device.

In another embodiment, the compound of Formula (I) may have the following Formula (III)

(III)

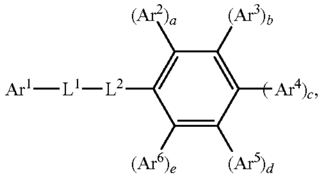

According to another aspect of the present invention $L^1$ represents a single bond in compound of Formula (III).

According to another aspect of the present invention $L^2$ in the compound of Formula (III) is a substituted or unsubstituted $C_6$ to $C_{30}$ arylene group.

According to another aspect of the present invention $L^2$ in the compound of Formula (II) is $C_3$ to $C_{25}$ heteroarylene group.

In this way, it is possible to farther improve the relevant properties of the compound of Formula (I) regarding LUMO, dipole moment, melting point and rate onset temperature and to farther improve the performance of the organic electronic device.

According to another aspect of the present invention, $Ar^1$ is a substituted or unsubstituted $C_{16}$ to $C_{36}$ condensed aryl group comprising at least four fused rings and at least two of the fused rings share at least two carbon atoms with each other, wherein the one or more substituent(s), if present in $Ar^1$, are independently selected from the group consisting of $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, $PY(R)_2$, wherein, Y being O or S, R are independently selected from $C_1$-$C_{20}$ linear alkyl, $C_1$-$C_{20}$ alkoxy, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_6$-$C_{20}$ aryl and $C_3$-$C_{20}$ heteroaryl.

According to another aspect of the present invention, $L^2$ a substituted or unsubstituted $C_6$ to $C_{30}$ arylene group, substituted or unsubstituted $C_3$ to $C_{25}$ heteroarylene group, wherein the one or more substituent(s), if present in $L^2$, are independently selected from the group consisting of $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, $PY(R)_2$, wherein, Y being O or S, R are independently selected from $C_1$-$C_{20}$ linear alkyl, $C_1$-$C_{20}$ alkoxy, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_6$-$C_{20}$ aryl and $C_3$-$C_{20}$ heteroaryl.

According to another aspect of the present invention, $Ar^2$, $Ar^3$, $Ar^4$, $Ar^5$ and $Ar^6$ are independently selected from the group consisting of substituted or unsubstituted $C_6$ to $C_{30}$ aryl, substituted or unsubstituted $C_2$ to $C_{30}$ heteroaryl, wherein the one or more substituent(s), if present in one or more of the group $Ar^2$, $Ar^3$, $Ar^4$, $Ar^5$ and $Ar^6$, are independently selected from the group consisting of D, F, CN, $C_1$ to $C_{16}$ alkyl, $C_1$ to $C_{16}$ alkoxy, nitrile, $PY(R)_2$, wherein, Y being O or S, R are independently selected from $C_1$-$C_{20}$ linear alkyl, $C_1$-$C_{20}$ alkoxy, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_6$-$C_{20}$ aryl and $C_3$-$C_{20}$ heteroaryl.

$Ar^1$ may be selected from the group consisting of tetracenyl, fluoranthenyl, pyrenyl and chrysenyl. In this way, it is possible to farther improve the relevant properties of the compound of Formula (I) regarding LUMO, dipole moment, melting point and rate onset temperature and to further improve the performance of the organic electronic device.

$L^1$ may represent a single bond or may be selected from phenylene, diphenylene, triphenylene and naphthylene. In particular $L^1$ may be selected from one of the following moieties A-1 to A-12.

A-1

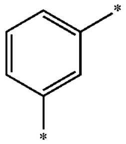

A-2

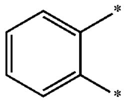

A-3

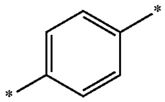

A-4

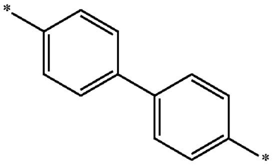

A-5

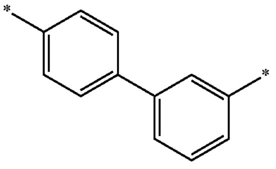

A-6

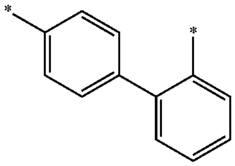

A-7

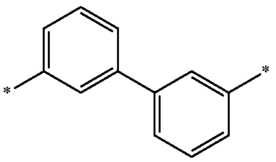

A-8

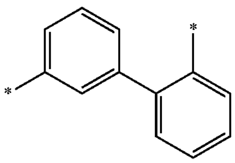

A-9

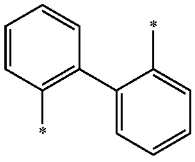

-continued

A-10

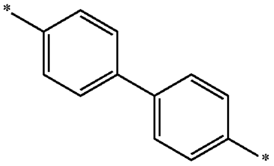

A-11

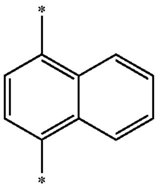

A-12

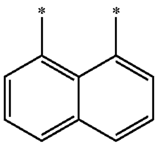

wherein the asterisk symbol "*" represents the binding positions of $L^1$.

According to another aspect of the present invention the compound of formula 1 wherein, $L^1$ may be preferably selected from group comprising A-1 to A-4 or A-10 to C-12. According to another aspect of the present invention the compound of formula 1 wherein, $L^1$ may be more preferably selected from group comprising A-5 to A-9 or A-10 to C-12.

$L^2$ may be selected from substituted or unsubstituted phenylene, substituted or unsubstituted biphenylene, substituted or unsubstituted triphenylene and substituted or unsubstituted naphthylene. In particular $L^2$ may be selected from one of the following moieties B-1 to B-18.

B-1

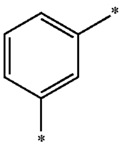

B-2

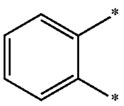

B-3

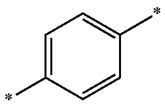

B-4

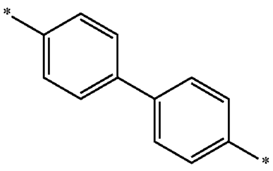

-continued

B-5

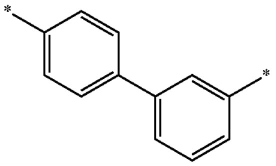

B-6

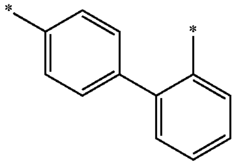

B-7

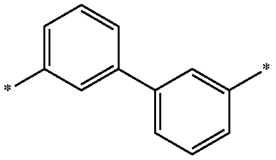

B-8

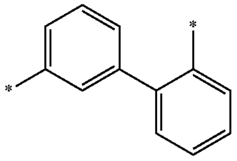

B-9

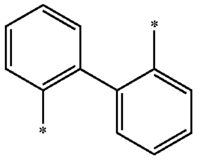

B-10

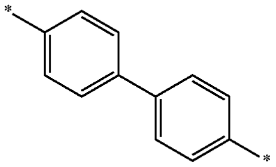

B-11

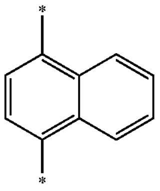

B-12

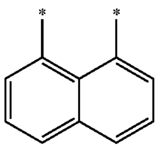

B-13

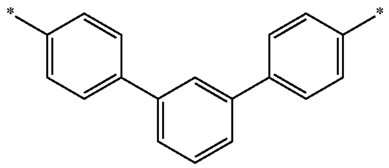

-continued

B-14

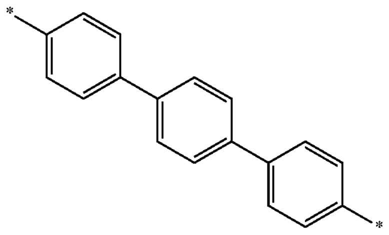

B-15

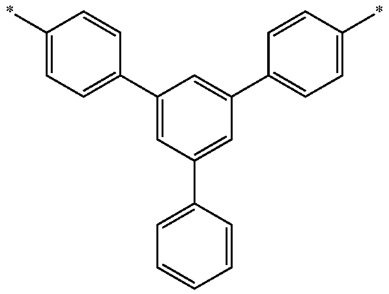

B-16

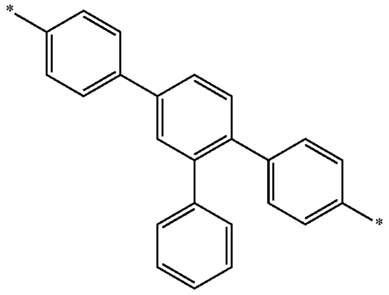

B-17

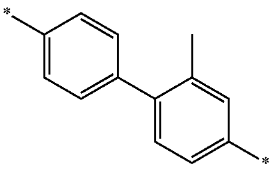

B-18

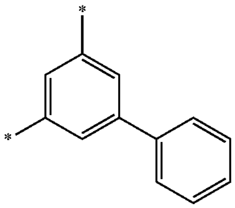

wherein the asterisk symbol "*" represents the binding positions of $L^2$.

In the compound of formula 1, $L^1$ may be preferably selected from group comprising B-1 to B-3 or B-9 to B-18. In the compound of formula 1, $L^1$ may be more preferably selected from group comprising 8-4 to B-12 or B-13 to B-18.

In this way, it is possible to further improve the relevant properties of the compound of Formula (I) regarding LUMO, dipole moment, melting point and rate onset temperature and to further improve the performance of the organic electronic device.

With respect to the inventive compound, a, b, c, d and e are independently selected from 0 or 1, and $2 \leq a+b+c+d+e \leq 5$ preferably $2 \leq a+b+c+d+e \leq 4$. In this way, it is possible to further improve the relevant properties of the compound of Formula (I) regarding LUMO, dipole moment, melting point and rate onset temperature and to farther improve the performance of the organic electronic device.

According to another aspect of the present invention, $Ar^2$, $Ar^3$, $Ar^4$, $Ar^5$ and $Ar^6$ are independently selected from the group consisting of substituted or unsubstituted $C_6$ to $C_{30}$ aryl, substituted or unsubstituted $C_2$ to $C_{3Q}$ heteroaryl. In particular $Ar^2$, $Ar^3$, $Ar^4$, $Ar^5$ and $Ar^6$ may be selected from one of the fallowing moieties C-1 to C-12.

C-1

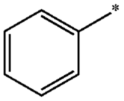

C-2

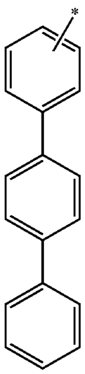

C-3

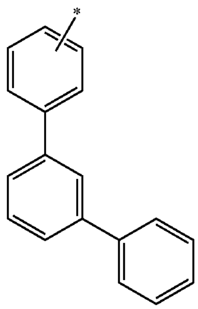

C-4

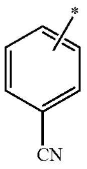

C-5

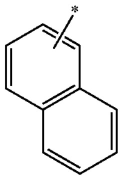

C-6

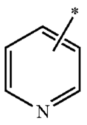

-continued

C-7

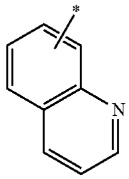

C-8

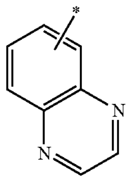

C-9

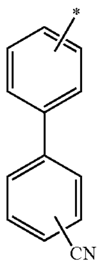

C-10

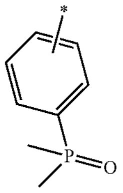

C-11

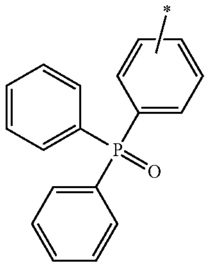

C-12

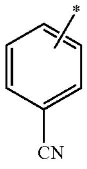

wherein the asterisk symbol "*" represents the binding position of $Ar^2$, $Ar^3$, $Ar^4$, $Ar^5$ and $Ar^6$.

According to another aspect of the present invention the compound of formula 1, $Ar^2$, $Ar^3$, $Ar^4$, $Ar^5$ and $Ar^6$ can be independently selected preferably from group comprising C-1 to C-5 and C-12 to C-15. According to another aspect of the present invention the compound of formula 1, $Ar^2$, $Ar^3$, $Ar^4$, $Ar^5$ and $Ar^6$ can be independently selected more preferably from group comprising C-1 to C-5 and C-8 to C-11 and C-12 to C-13. According to another aspect of the present invention the compound of formula 1, $Ar^8$, $Ar^3$, $Ar^4$, $Ar^5$ and $Ar^6$ can be independently selected most preferably from group comprising C-1 to C-5.

According to another aspect of the present invention, at least two of $Ar^2$, $Ar^3$, $Ar^4$, $Ar^5$ and $Ar^6$ are selected same when 2≤a+b+c+d+e≤5, preferably at least three of $Ar^2$, $Ar^3$, $Ar^4$, and $Ar^5$ are selected same when 2≤a+b+c+d+e≤5, further preferred at least four of $Ar^2$, $Ar^3$, $Ar^4$, and $Ar^5$ are selected same when 2≤a+b+d+e≤5.

According to another aspect of the present invention the compound of formula 1 is free of a carbazole, indolocarbazole and/or fluorene group.

Furthermore, the compound of Formula (I) may be selected from one of the following compounds D-1 to D-30 or E-1 to E-8.

D-1

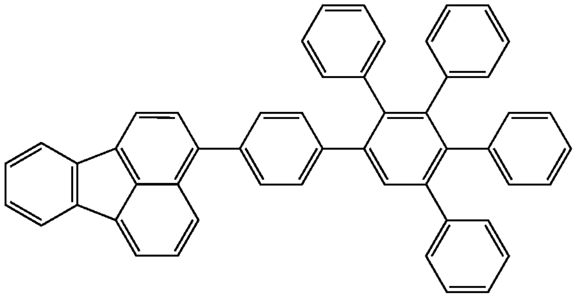

D-2

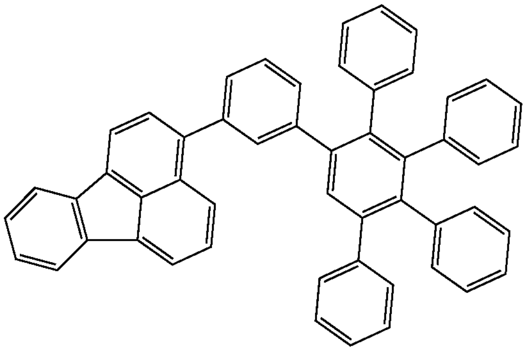

D-3

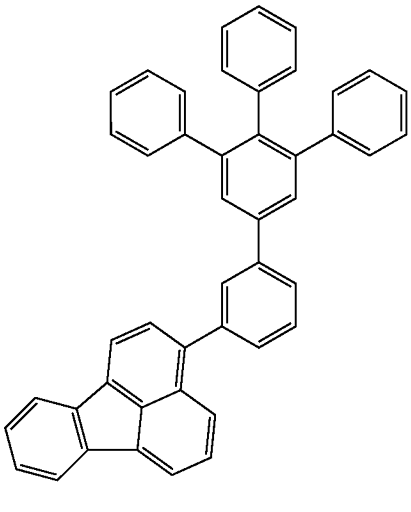

-continued

D-4

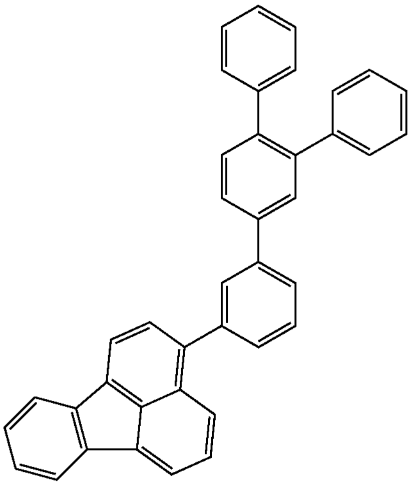

D-5

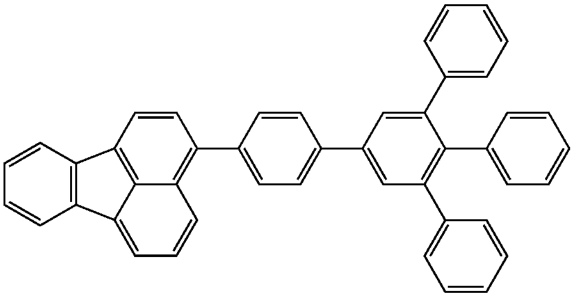

D-6

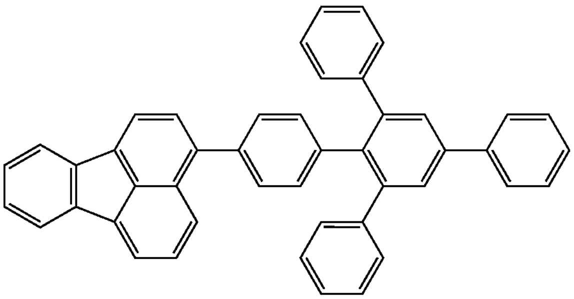

D-7

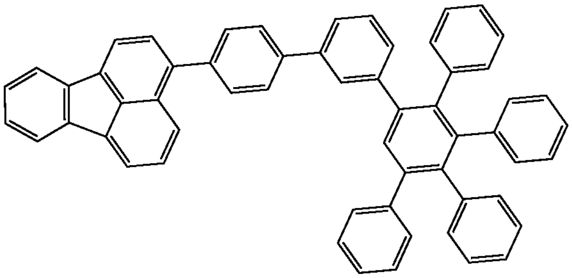

D-8

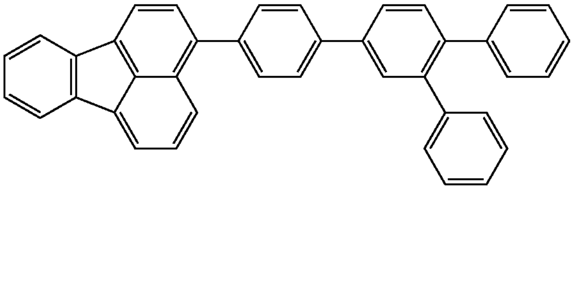

-continued
D-9
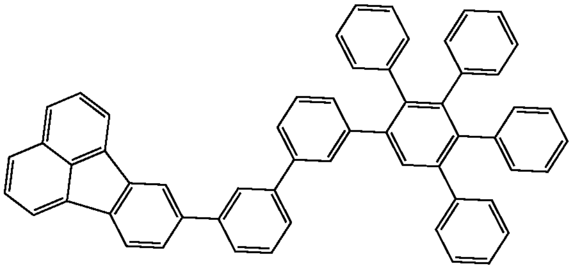
D-10
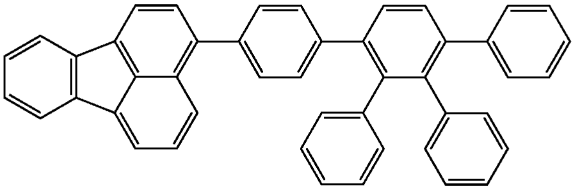
D-11
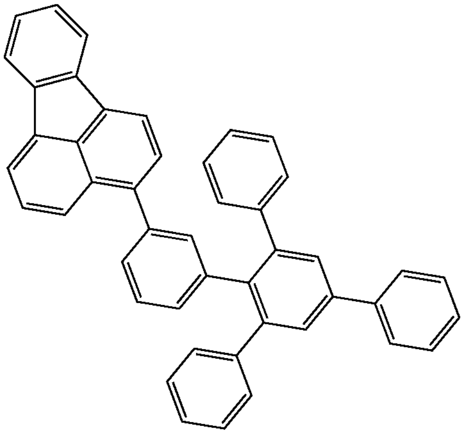
D-12
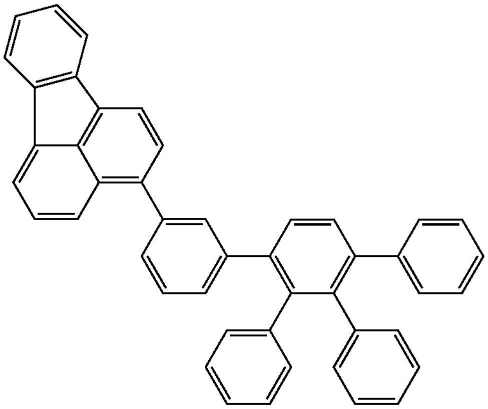
-continued
D-13
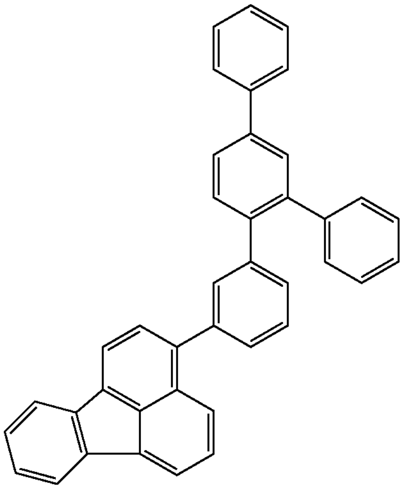
D-14
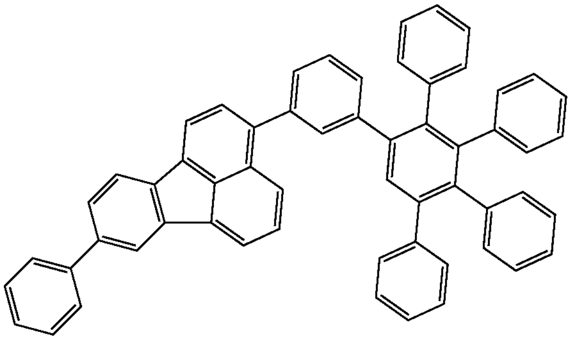
D-15
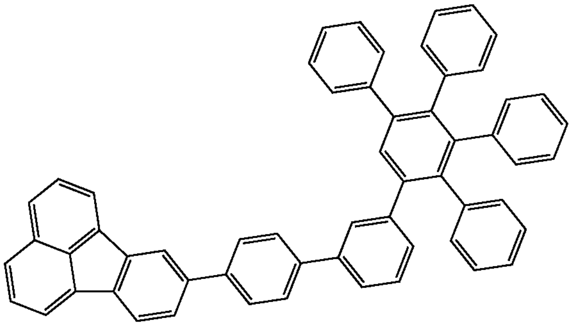
D-16
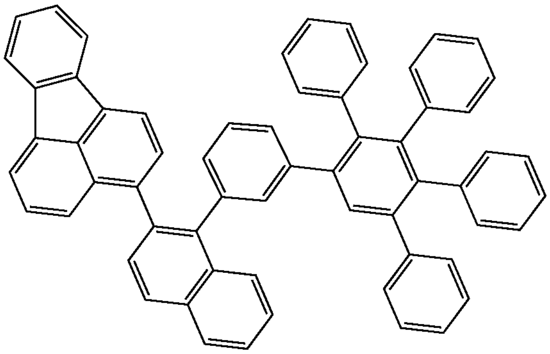

-continued
D-17
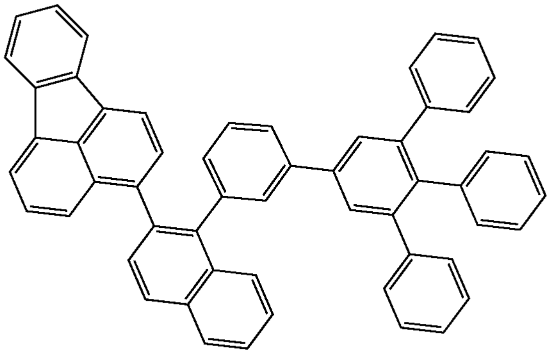
D-18
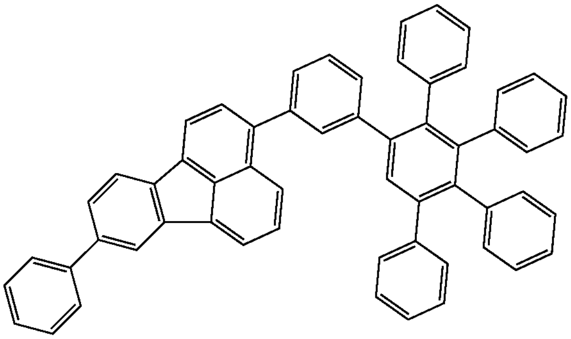
D-19
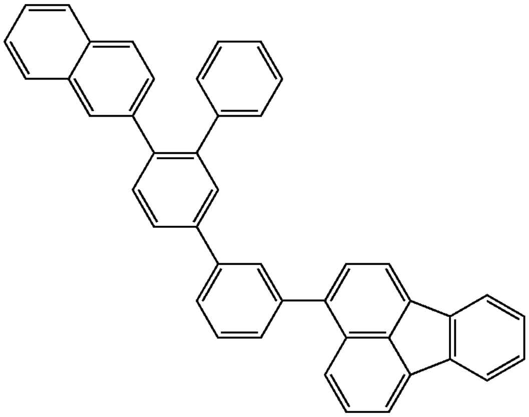
D-20
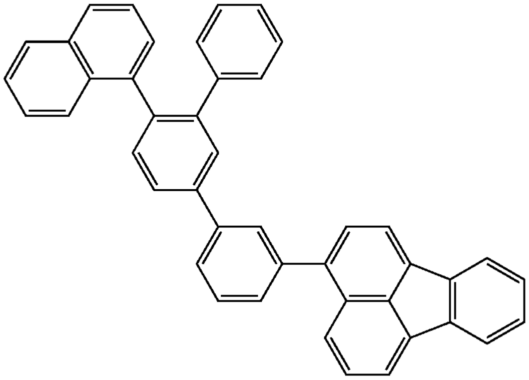
-continued
D-21
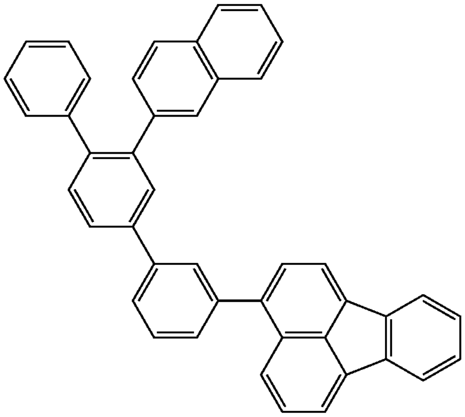
D-22
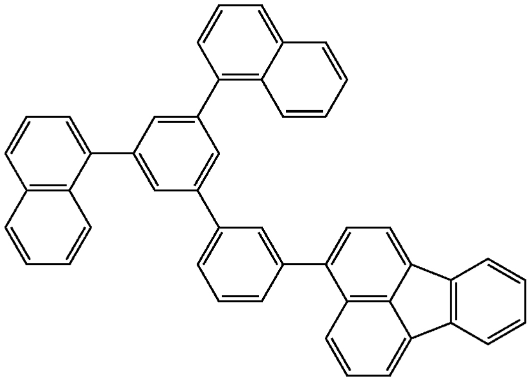
D-23
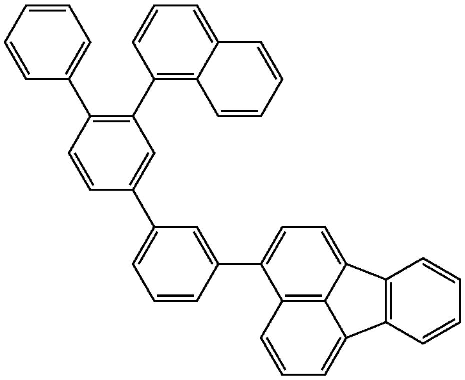
D-24
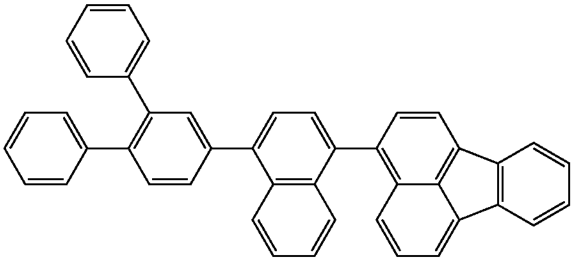

-continued
D-25
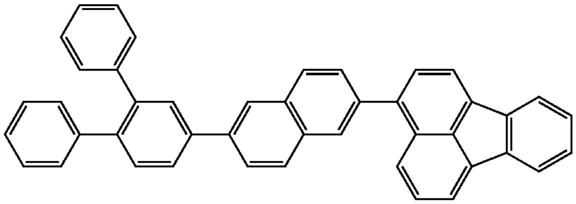
D-26
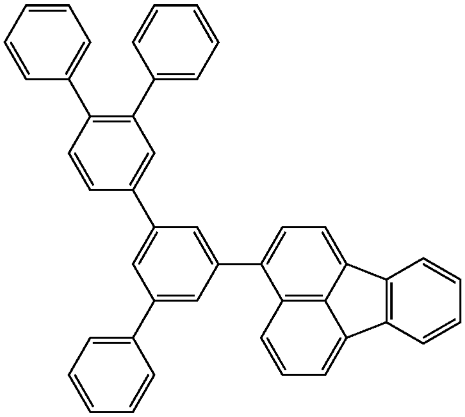
D-27
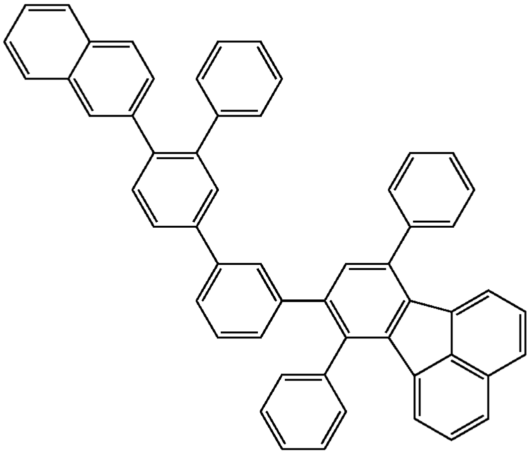
D-28
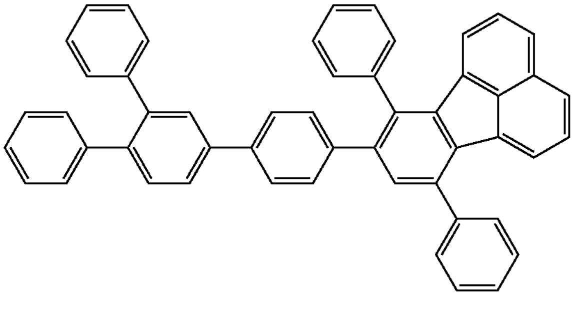
-continued
D-29
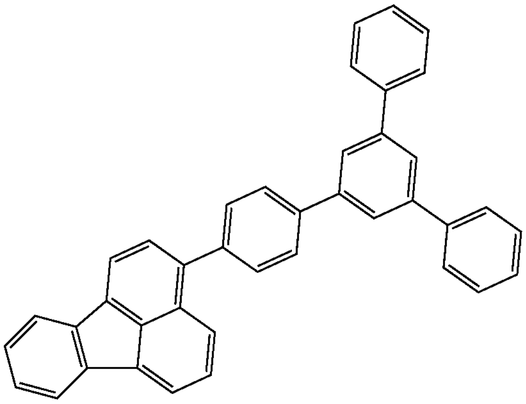
D-30
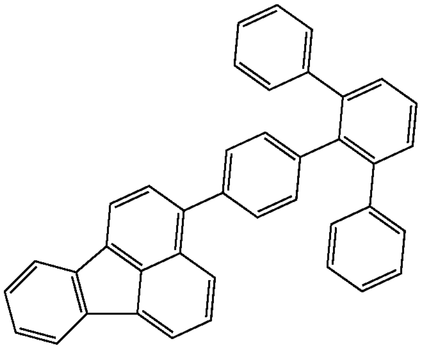
D-31
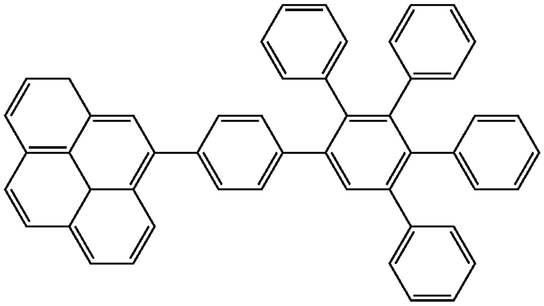
D-32
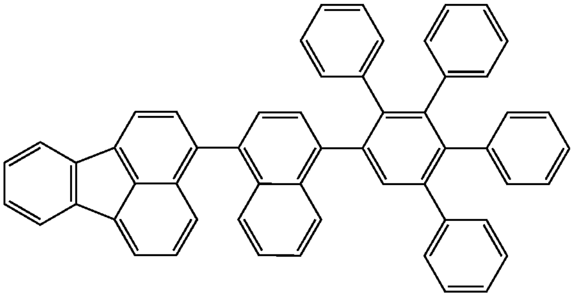

-continued
D-33
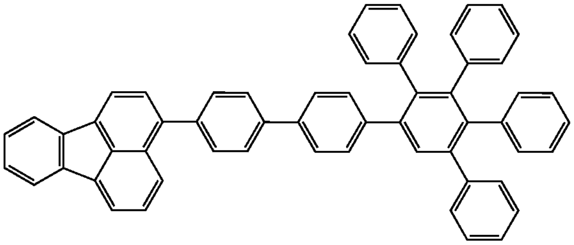
E-1
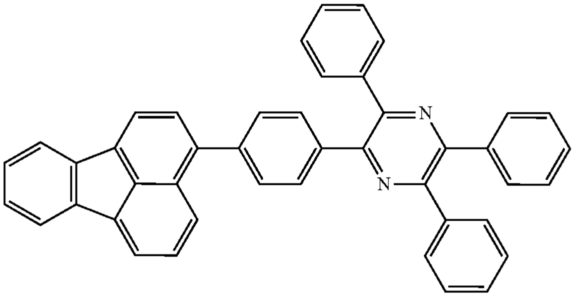
E-2
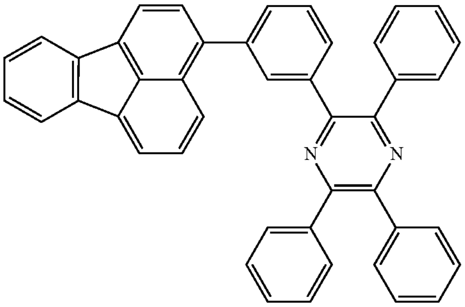
E-3
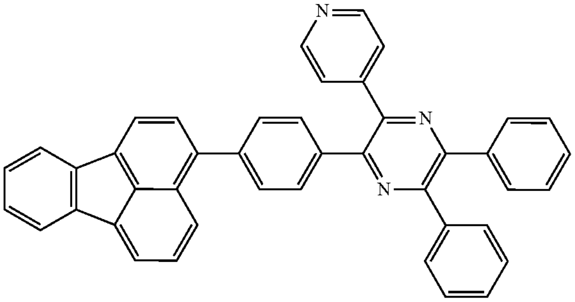
-continued
E-4
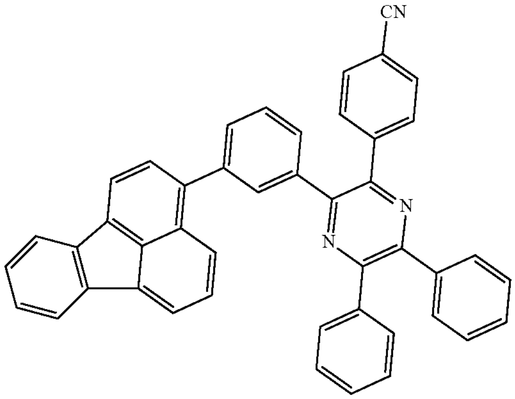
E-5
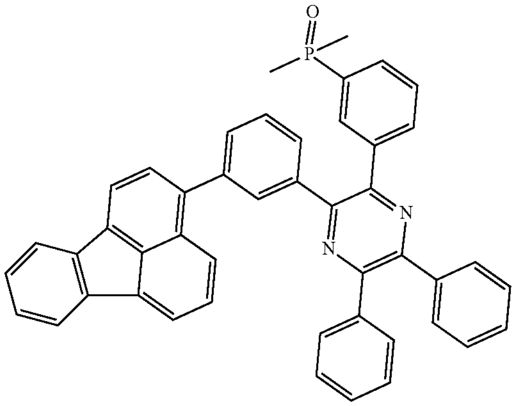
E-6
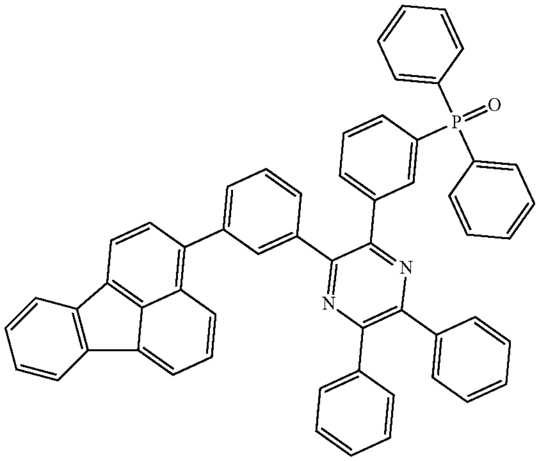

-continued

E-7

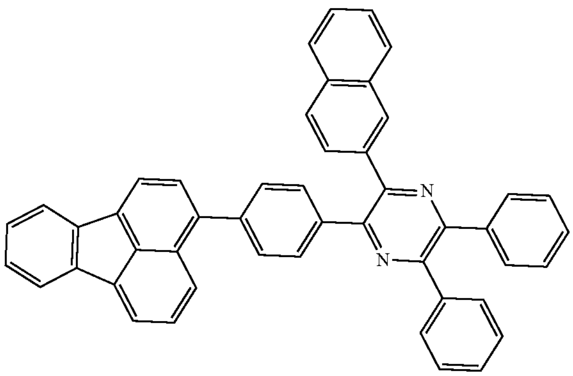

E-8

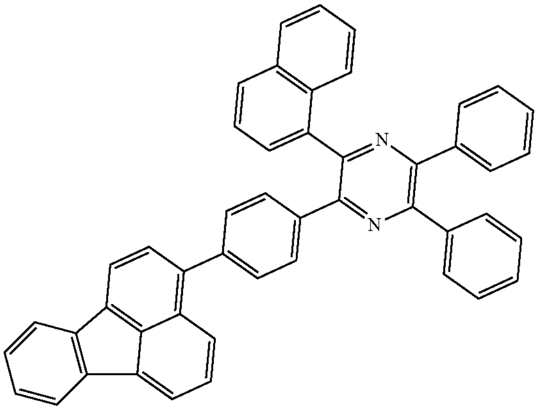

According to another aspect of the present invention, the hydrogen atoms in the compound of formula (I) may be partially or fully replaced by halogen atoms.

According to another aspect of the present invention, the hydrogen atoms in lie compound of formula (I) may be partially or fully replaced by deuterium, atoms and/or fluorine atoms.

In this way, it is possible to further improve the relevant properties of the compound of Formula (I) regarding LUMO, dipole moment, melting point and rate onset temperature and to further improve the performance of the organic electronic device.

The object is further achieved by an organic semiconducting layer comprising the compound of Formula (I) as defined herein.

In this regard, it may be provided that the organic semiconducting layer consists of the compound of Formula (I).

The organic semiconducting layer may further comprise a metal, a metal salt or an organic metal complex, alternatively an alkali metal complex and/or an alkaline earth metal complex.

The organic semiconducting layer may be non-emissive.

The object is further achieved by an organic electronic device comprising the organic semiconducting layer as defined herein.

The organic electronic device may further comprise an emission layer an anode and a cathode, wherein the organic semiconducting layer is arranged between the emission layer and the cathode, preferably in direct contact with the emission layer.

ID this regard, it may be provided that the organic semiconducting layer in the organic electronic device is an auxiliary ETL, respectively a hole blocking layer.

The organic electronic device may further comprise an electron transport layer, wherein the organic semiconducting layer is contacting sandwiched between the emission and the electron transport layer.

The object is farther achieved by a display device comprising the organic electronic device as defined herein.

The object is farther achieved by a lighting device comprising the organic electronic device as defined herein.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide ($SnO_2$), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MTDATA), TDATA, 2T-NATA, polyaniline/dodecylbenzenesulfonic add (Pani/DBSA), poly(3,4-ethylenedioxythiophene)/poly(4-styrenesulfonate)

(PEDOT/PSS), polyaniline/camphor sulfonic add (Pani/CSA), and polyaniline)/poly(4-styrenesulfonate (PANI/PSS).

The HIL may comprise or consist of p-type dopant and the p-type dopant may be selected from tetrafluoro-tetracyanoquinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant Typical examples of known doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO=−5.2 eV) doped with F4TCNQ; α-NPD (N,N-Bis(naphthalen-1-yl)-N,N'-bis(phenyl)-benzidine) doped with F4TCNQ. α-NPD doped with 2,2'-(perfluoronaphthalen-2,6-diylidene) dimalononitrile. The p-type dopant concentrations can be selected from 1 to 20 wt-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin mating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are; carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about too nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylamine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

It may be provided that the emission layer does not comprise the compound of Formula (I).

The emission layer (EML) may be formed of a combination of a host and an emitter dopant. Example of the host are Alq3, 4,4'-N,N'-dicarbazole-biphenyl (CBP), poly(n-vinylcarbazole) (PVK), 9,10-di(naphthalene-2-yl)anthracene (ADN), 4,4',4"-tris(carbazol-9-yl)-triphenylamine(TCTA), 1,3,5-tris(N-phenylbenzimidazole-2-yl)benzene (TPBI), 3-tert-butyl-9,10-di-2-naphthylanthracene (TBADN), distyrylarylene (DSA) and bis(2-(2-hydroxyphenyl)benzothiazolate)zinc (Zn(BTZ)2).

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4,4'-bis(4-diphenyl aminostyryl)biphenyl (DPAVBi), 2,5,8,11-tetra-tert-butyl perylene (TBPe) are examples of fluorescent blue emitter dopants.

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer may be the inventive organic semiconducting layer comprising or consisting of the inventive compound represented by the general Formula (I) as defined above.

The HBL may also be named auxiliary ETL or a-ETL and electron transport layer 1 or ETL-1.

The electron transport layer 1 of the organic electronic device may comprise the compound represented by general Formula (I)

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include xadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with one preferred embodiment of the invention, the electron transport layer may be the inventive organic semiconducting layer comprising the inventive compound represented by the general Formula (I) as defined herein.

According to various embodiments the OLED may comprise an electron transport layer or an electron transport layer stack comprising at least a first electron transport layer and at least a second electron transport layer.

By suitably adjusting energy levels of particular layers of the ETL, the injection, and transport of the electrons may be controlled, and the holes may be efficiently blocked. Thus, the OLED may have long lifetime.

The electron transport layer of the organic electronic device may comprise the compound represented by general Formula (I) as defined above as the organic electron transport matrix (ETM) material. The electron transport layer may comprise, besides or instead of the compound represented by the general Formula (I), further ETM materials known in the art. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined below.

Further, the organic semiconducting layer may comprise one or more n-type dopants. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolatolithium (LiQ), Lithium tetra(1H-pyrazol-1-yl)borate or Lithium 2-(diphenylphosphoryl)phenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP1970 371 A1 or WO 2013/079217 A1.

According to another aspect of the present invention organic semiconducting layer may comprise one or more alkali metal salt and alkali metal organic complex

- the alkali metal salt is selected from the group comprising LiF, LiCl, LiBr or LiI, and preferably LiF;
- the alkali metal organic complex is selected from the group comprising a lithium quinolinolate, lithium borate, lithium phenolate, lithium pyridinolate or comprises a lithium with a Schiff base ligand;
- preferably the lithium quinolinolate complex has the formula IV, V or VI:

(IV)

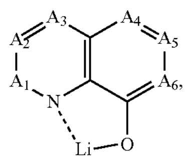

(V)

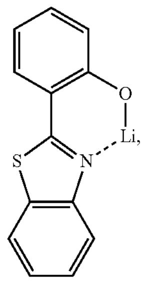

(VI)

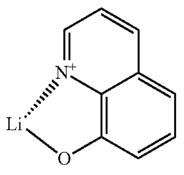

wherein

- $A_1$ to $A_6$ are same or independently selected from CH, CR, N, O;
- R is same or independently selected from hydrogen, halogen, alkyl or aryl or heteroaryl with 1 to 20 carbon atoms; and more preferred A1 to A6 are CH;
- preferably the borate based organic ligand is a tetra(1H-pyrazol-1-yl)borate;
- preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;

preferably the pyridinolate is a 2-(diphenylphosphoryl) pyridin-3-olate, preferably the lithium Schiff base has the structure 100, 101, 102 or 103:

100

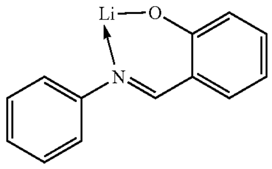

101

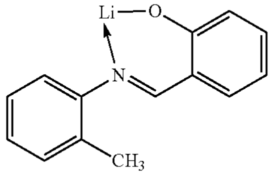

102

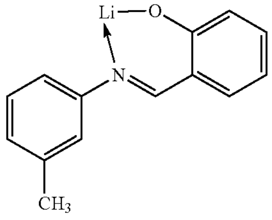

103

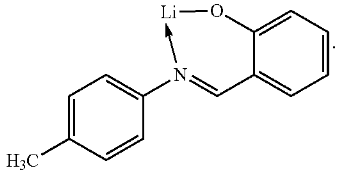

According to another aspect of the present invention, the OLED may comprise an electron transport layer or an electron transport layer stack comprising at least a first electron transport layer and at least a second electron transport layer wherein the first electron transport layer may comprise the compound represented by general Formula (I).

Electron Injection Layer (EIL)

An optional EIL, which may facilitates injection of electrons from the cathode, may be formed on EIL include lithium 8-hydroxyquinolinolate (LiQ), LiF, NaCl, CsF, Li2O, BaO, Ca, Ba, Yb, Mg which are known in the art Deposition and coating conditions for forming the EIL are similar to those for formation of the HIL, although the deposition and coating conditions may vary, according to the material that is used to form the EIL. The ETL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, the cathode electrode may be transparent or semitransparent even if formed from a metal or metal alloy.

It is to be understood that the cathode electrode is not part of an electron injection layer or the electron transport layer.

Charge Generation Layer/Hole Generating Layer

The charge generation layer (CGL) may comprise a p-type and an n-type layer. An interlayer may be arranged between the p-type layer and the n-type layer.

Typically, the charge generation layer is a pn junction joining an n-type charge generation layer (electron generating layer) and a hole generating layer. The n-side of the pn junction generates electrons and injects them into the layer which is adjacent in the direction to the anode.

Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, FeCl3, $FeF_3$, and SbCl5. Also, the host can be one selected from a group consisting of N,N'-di(naphthalen-1-yl)-N,N-diphenyl-benzidine (NPB), N,N'-diphenyl-N,N'-bis(3-methylphenyl)-1,1-biphenyl-4,4-diamine (TPD) and N,N',N'-tetranaphthyl-benzidine (TNB), The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Electronic Device

An organic electronic device according to the invention comprises an organic semiconducting layer comprising a compound according to Formula (I).

An organic electronic device according to one embodiment may include a substrate, an anode layer, an organic semiconducting layer comprising a compound of Formula (I) and a cathode layer.

An organic electronic device according to one embodiment comprises at least one organic semiconducting layer comprising at least one compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using;

at least one deposition source, preferably two deposition sources and more preferred at least three deposition sources.

The methods for deposition that can be suitable comprise:

deposition via vacuum thermal evaporation;

deposition via solution processing, preferably the processing is selected from spin-coating, printing, casting; and/or slot-die coating.

According to various embodiments of the present invention, there is provided a method using:

a first deposition source to release the compound of Formula (I) according to the invention, and a second deposition source to release the metal, a metal salt or an alkali or alkaline earth metal complex; alternatively an organic alkali or alkaline earth metal complex; alternatively 8-hydroxyquinolinolato lithium or alkali borate;

the method comprising the steps of forming the organic semiconducting layer; whereby for an organic light-emitting diode (OLED):

the organic semiconducting layer is formed by releasing the compound of Formula (I) according to the invention from the first deposition source and a metal, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may farther include the steps for forming an organic light-emitting diode (OLED), wherein on a substrate a first anode electrode is formed, on the first anode electrode an emission layer is formed, on the emission layer an electron transport layer stack is formed, optionally a hole blocking layer is formed on the emission layer and an organic semiconducting layer is formed, and finally a cathode electrode is formed, optional a hole injection layer, a hole transport layer, and a hole blocking layer, formed in that order between the first anode electrode and the emission layer, optional an electron injection layer is formed between the organic semiconducting layer and the cathode electrode.

According to various embodiments of the present invention, the method may farther comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:

anode, hole injection layer, first hole transport layer, second hole transport layer, emission layer, optional hole blocking layer, organic semiconducting layer comprising a compound of Formula (I) according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

(XX)

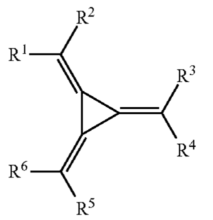

(XXIa)

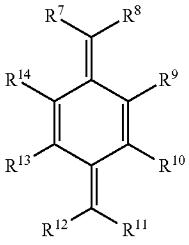

(XXIb)

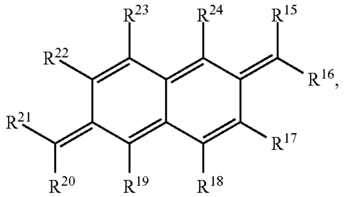

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ axe independently selected from above mentioned electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

Details and Definitions of the Invention

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and isopropyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthracene, tetracene etc. Further encompassed are biphenyl and oligo- or polyphenyls, such as terphenyl etc. Further encompassed shall be any further aromatic hydrocarbon substituents, such as fluorenyl etc. "Arylene" respectively "heteroarylene", refers to groups to which two further moieties are attached. In the present specification the term "aryl group" or "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The aryl or arylene group may include a monocyclic or fused ring polycyclic (i.e., rings sharing adjacent pairs of carbon atoms) functional group.

The term "condensed aryl(ene) group" as to an aryl group comprising at least two aromatic rings which are fused to each other by sharing two carbon atoms with each other. In this regard, it may be provided that the condensed aryl group (or the condensed arylene group) comprises more than two fused rings wherein each of the rings is fused with at least one other aryl ring of the condensed aryl(ene) by sharing with this one (or more) further ring(s) two carbon atoms. Non-limiting examples of such condensed aryl groups are fluoranthenyl, chrysenyl, pyrenyl etc.

The term "alkenyl" as used herein refers to a group $—CR^1{=}CR^2R^3$ comprising a carbon-carbon double bond.

The term "perhalogenated" as used herein refers to a hydrocarbyl group wherein all of the hydrogen atoms of the hydrocarbyl group are replaced by halogen (F, Q, Br, I) atoms.

The term "alkoxy" as used herein refers to a structural fragment of the Formula —OR with R being hydrocarbyl, preferably alkyl or cycloalkyl.

The term "heteroaryl" as used herein refers to aryl groups in which at least one carbon atom is substituted with a heteroatom, preferably selected from N, O, S, B or Si.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably a heteroarylene ring may comprise at least 1 to 3 heteroatoms individually selected from N, S and/or O.

The term "heteroaryl" as used herewith shall encompass pyridine, quinoline, benzoquinoline, quinazoline, benzoquinazoline, pyrimidine, pyrazine, triazine, benzimidazole, benzothiazole, benzo[4,5]thieno[3,2-d]pyrimidine, carbazole, xanthene, phenoxazine, benzoacridine, dibenzoacridine and the like.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconductive layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into spare in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by too. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about a ≥380 nm to about ≤780 nm.

Preferably, the organic semiconducting layer comprising the compound of Formula (I) is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milliAmpere per square centimeter (mA/cm2).

The external quantum efficiency, also named EQE, is measured in percent (96).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode j cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
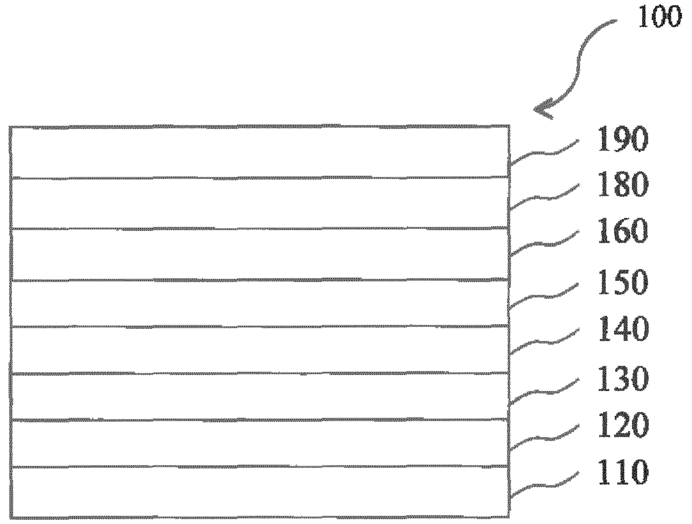
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate no, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
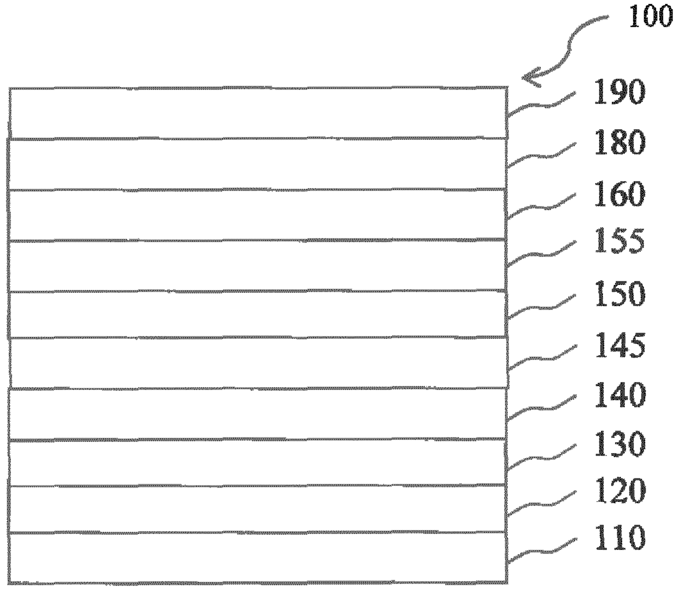
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) may be an HBL.

Figure 3:
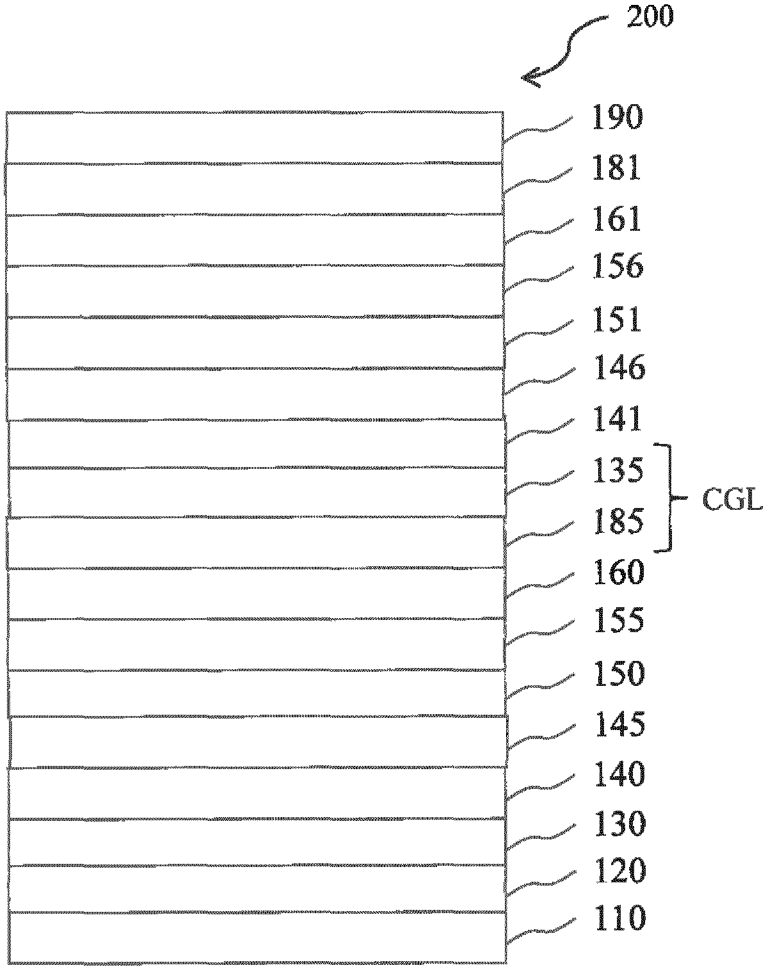
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate 110, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) may be the first ETL, e-type CGL and/or second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Experimental Data

Preparation of Compounds of Formula (I)

Compounds of formula (I) may be synthesized as shown below.

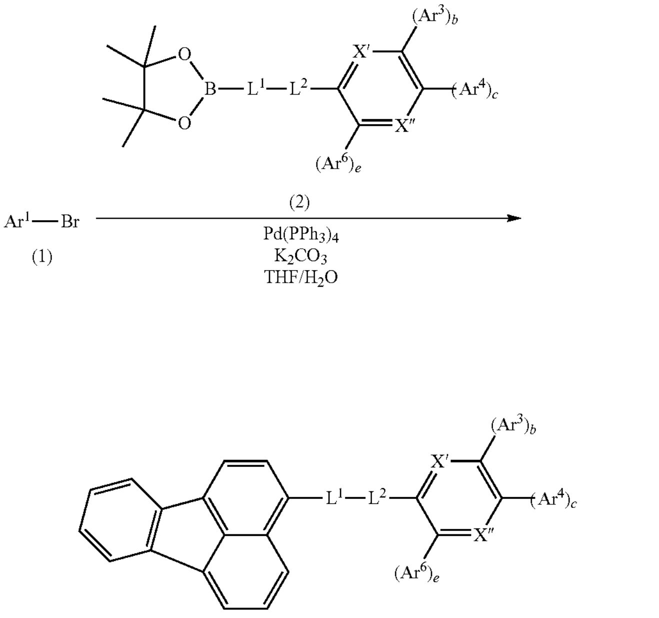

(D)

A flask was flushed with nitrogen and charged with compound (1) (49.8 mmol), compound (2) (54.8 mmol), $Pd(PPh3)_4$ (1.0 mmol), and potassium carbonate (99.6 mmol). A mixture of deaerated THF/water (4:1, 300 mL) was added and the reaction mixture was heated to 75° C. under a nitrogen atmosphere overnight. After cooling down to room temperature, solvents were removed under reduced pressure. Resulting crude was dissolved in dichloromethane (400 mL) and the organic phase was washed first with NaDTC(aq.) (3×300 mL) and the with water (3×300 mL). After drying over $MgSO_4$, the organic phase was filtered through a florisil pad. After rinsing with additional dichloromethane (1000 mL), the filtrate was concentrated under reduced pressure to a minimal volume and acetonitrile (350 mL) was added. The precipitate was collected by suction filtration and dissolved again in dichloromethane (400 mL) and the solution was concentrated under reduced pressure to a minimal volume and acetonitrile (300 mL) was added.

The precipitate was collected by suction filtration to yield compound D (compound of formula 1) after drying. Final purification was achieved by sublimation.

Synthesis of 3-(3',4',5'-triphenyl-[1,1':2',1"-terphenyl]-4-yl)fluoranthene (D-1)

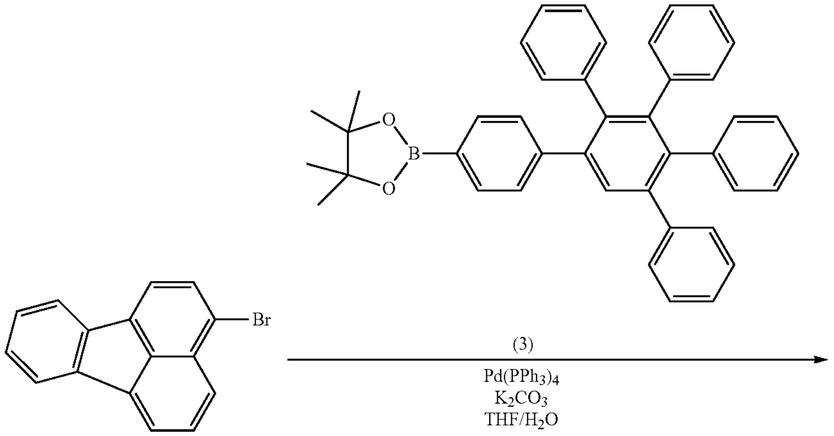

(1')

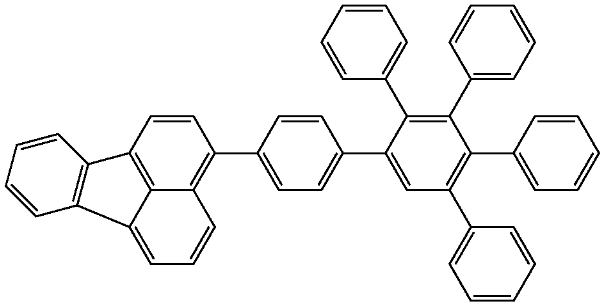 [SMILES: c1ccc(-c2cc(-c3ccc(-c4ccc5c6c(cccc46)-c4ccccc4-5)cc3)c(-c3ccccc3)c(-c3ccccc3)c2-c2ccccc2)cc1]

(D-1)

To synthesis compound D-1 a flask was flushed with nitrogen and charged with 3-bromofluoranthene (1') (14.0 g, 49.8 mmol), 4,4,5,5-tetramethyl-2-(3',4',5'-triphenyl-[1,1':2',1"-terphenyl]-4-yl)-1,3,2-dioxaborolane (3) (32.0 g, 54.3 mmol), $Pd(PPh3)_4$ (1.2 g, 1.0 mmol), and potassium carbonate (13.8 g, 99.6 mmol). A mixture of deaerated THF/water (4:1, 300 mL) was added and the reaction mixture was heated to 75° C. under a nitrogen atmosphere overnight. After cooling down to room temperature, solvents were removed under reduced pressure. Resulting crude was dissolved in dichloromethane (400 mL) and the organic phase was washed first with NaDTC(aq.) (3×300 mL) and the with water (3×300 mL). After drying over $MgSO_4$, the organic phase was filtered through a florisil pad. After rinsing with additional dichloromethane (1000 mL), the filtrate was concentrated under reduced pressure to a minimal volume and acetonitrile (350 mL) was added. The precipitate was collected by suction filtration and dissolved again in dichloromethane (400 mL) and the solution was concentrated under reduced pressure to a minimal volume and acetonitrile (300 mL) was added. The precipitate was collected by suction filtration to yield 28.2 g of C-1 after drying. Final purification was achieved by sublimation, m/z=658 ($M^+$).

Synthesis of 3-(3',4',5'-triphenyl-[1,1':2',1"-terphenyl]-3-yl)fluoranthene (D-2)

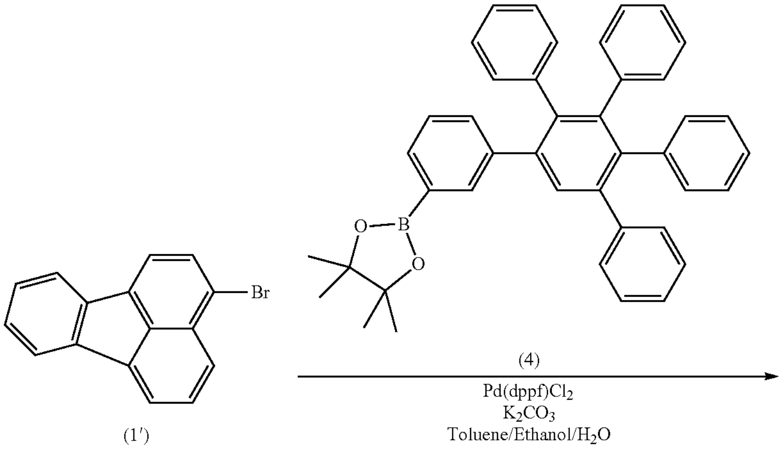

(1') (4)

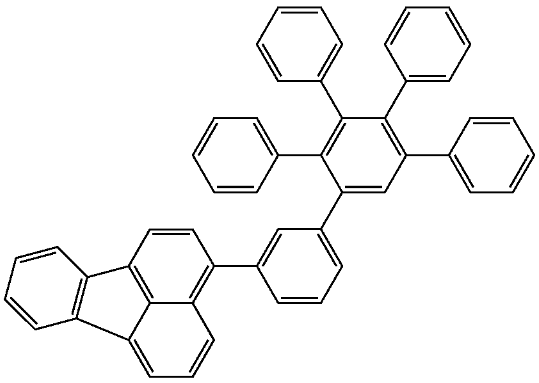

(D-2)

To synthesis compound C-2 a flask was flushed with nitrogen and charged with 3-bromofluoranthene (1') (14.0 g, 49.8 mmol), 4,4,5,5-tetramethyl-2-(3',4',5'-triphenyl-[1,1':2',1"-terphenyl]-3-yl)-1,3,2-dioxaborolane (4) (30.6 g, 52.3 mmol), Pd(dppf)Cl2 (0.18 g, 0.25 mmol), and potassium carbonate (13.8 g, 99.6 mmol), A mixture of deaerated Toluene/Ethanol/water (10:1:5, 320 mL) was added and the reaction mixture was heated to 70° C. under a nitrogen atmosphere for 2 hours. After cooling down to room temperature, crude reaction solution was washed with water (1×50 mL). After drying over $MgSO_4$, the organic phase was filtered through a florisil pad. After rinsing with additional toluene (100 mL), the filtrate was concentrated under reduced pressure to 100 mL and n-hexane (150 mL) was added. The precipitate was collected by suction filtration, triturated in cyclohexane (900 mL) and recrystallized in DMF (37 mL), Finally it was washed with isopropanol (2×40 mL) to yield 17.4 g of D-2 after drying. Final purification was achieved by sublimation, m/z=658 ($M^+$).

Synthesis of 2-(4-(fluoranthen-3-yl)phenyl)-3,5,6-triphenylpyrazine (E-1)

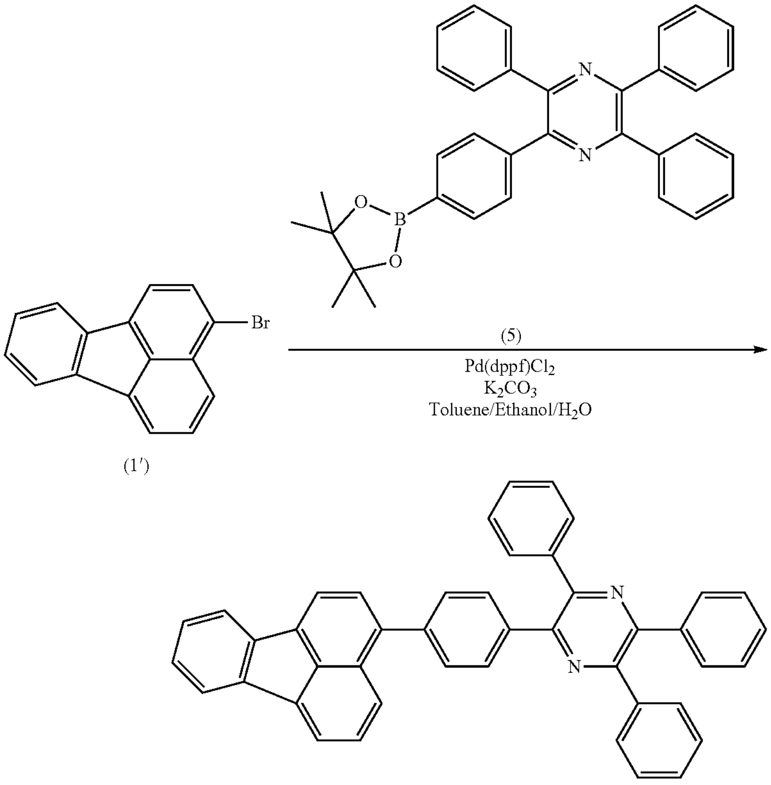

(E-1)

Compound (5) was obtained from 943442-81-7 via standard Suzuki-Miyaura conditions Compound (E-1) was synthesized analogue to (D-1) by reacting compound (1') (CAS 13438-50-1) with compound (5). 9.4 g (62%) of (E-1) were obtained after drying. Final purification was achieved by sublimation, m/z=585 (M+H+).

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

According to another aspect of the present invention the compound of formula (I) may have a melting point of about ≥200° C. and about ≤280° C., preferably about ≥210° C. and about ≤275° C., further preferred about a ≥215° C. and about ≤270° C.

Glass Transition Temperature

The glass transition temperature (Tg) is measured under nitrogen and using a heating rate of 10 K per min in a Mettler Toledo DSC 822c differential scanning calorimeter as described in DIN EN ISO 11357, published in March 2010.

According to another aspect of the present invention the compound of formula (I) According to another embodiment the compound of formula 1 may have a glass transition temperature Tg of about ≥115° C. and about ≤280° C., preferably about ≥130° C. and about ≤250° C., further preferred about ≥135° C. and about ≤220° C., in addition preferred about ≥140° C. and about ≤190° C.

Rate Onset Temperature

The rate onset temperature $T_{RO}$ is determined by loading 100 mg compound into a VTE source. As VTE source a point source for organic materials is used as supplied by Kurt J. Lesker Company (www.lesker.com) or CreaPhys GmbH (http://www.creaphys.com). The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Ångstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200° C. to 260° C., If the rate onset temperature is below 200° C. the evaporation may be too rapid and therefore difficult to control. If the rate onset temperature is above 260° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

The rate onset temperature is an indirect measure of the volatility of a compound. The higher the rate onset temperature the lower is the volatility of a compound.

According to another aspect of the present invention the compound of formula (I) may have a rate onset temperature $T_{RO}$ of about ≥200° C. and about ≤350° C., preferably about ≥220° C. and about ≤350° C., further preferred about ≥250° C. and about ≤300° C.

Pinole Moment

The dipole moment $|\vec{\mu}|$ of a molecule containing N atoms is given by:

$$\vec{\mu} = \sum_{i}^{N} q_i \vec{r_1}$$

$$|\vec{\mu}| = \sqrt{\mu_x^2 + \mu_y^2 + \mu_z^2}$$

where $q_1$ and $\vec{r_1}$ are the partial charge and position of atom i in the molecule.

The dipole moment is determined by a semi-empirical molecular orbital method.

The geometries of the molecular structures are optimized using the hybrid functional B3LYP with the 6-31G* basis set in the gas phase as implemented in the program package TURBOMOLE V6.5. If more than one conformation is viable, the conformation with the lowest total energy is selected to determine the bond lengths of the molecules.

Calculated HOMO and LUMP

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.

According to another aspect of the present invention the compound of formula (I) may have a HOMO energy level (eV) in the range from about −6.00 eV to about −4.50 eV, preferably from about −5.85 eV to about −5.00 eV.

According to another aspect of the present invention the compound of formula (I) may have a LUMO energy level (eV) in the range from about −2.30 eV to about −1.70 eV, preferably about −2.30 eV to about −1.77 eV, further preferred from about −2.20 eV to about −1.77 eV.

General Procedure for Fabrication of OLEDs

For top emission devices, inventive examples 1 and 2, and comparative example 1 in Table 2, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes. 100 nm Ag were deposited on the glass substrate at a pressure of $10^{-5}$ to $10^{-7}$ mbar to form the anode.

Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 2,2',2"-(cyclopropane-1,2,3-triylidene)tris(2-(p-cyanotetrafluorophenyl)acetonitrile) was vacuum deposited on the anode, to form a HIL having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a HTL having a thickness of 118 nm.

Then, N,N-bis(4-(dibenzo[b,d]furan-4-yl)phenyl)-[1,1':4',1"-terphenyl]-4-amine (CAS 1198399-61-9) was vacuum deposited on the HTL, to form an electron blocking layer (EBL) having a thickness of 5 nm.

Then, 97 vol-% H09 (Sun Fine Chemicals) as EML host and 3 vol.-% BD200 (Sun Fine Chemicals) as fluorescent blue dopant were deposited on the EBL, to form a blue-emitting EML with a thickness of 20 nm.

Then the auxiliary ETL was formed with a thickness of 5 nm by depositing the compound of formula 1 according to the inventive example 1 and example 2 and comparative compound 1 according to the comparative example 1 on the emission layer (EML).

Then, the electron transporting layer was formed on the auxiliary electron transport layer by depositing 7-(4-(4-([1,1'-biphenyl]-2-yl)-6-phenyl-1,3,5-triazin-2-yl)phenyl) dibenzo[c,h]acridine (ETM-1, CAS 2378599-81-4) with a the thickness of 31 nm. The electron transport layer comprises 50 wt-% matrix compound and 50 wt-% of LiQ, see Table 2.

Then, the electron injection layer was formed on the electron transporting layer by deposing Yb with a thickness of 2 nm.

Ag was evaporated at a rate of 0.01 to 1 Å/s at $10^{-7}$ mbar to form a cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine (CAS 1242056-42-3) was formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in cd/$m^2$ using an Instrument Systems CAS-140CT array spectrometer for each of the voltage values. The cd/A efficiency at 10 mA/cm2 is determined by interpolating the luminance-voltage and current-voltage characteristics, respectively.

Lifetime LT of the device is measured at ambient conditions (20° C.) and 30 mA/$cm^2$, using a Keithley 2400 sourcemeter, and recorded in hours.

The brightness of the device is measured using a calibrated photo diode. The lifetime LT is defined as the time till the brightness of the device is reduced to 97% of its initial value.

The light output in external efficiency EQE and power efficiency (lm/W efficiency) are determined at 10 mA/cm2 for top emission devices.

To determine the efficiency EQE in % the light output of the device is measured using a calibrated photodiode.

To determine the power efficiency in lm/W, in a first step the luminance in candela per square meter (cd/m2) is measured with an array spectrometer CAS140 CT from Instrument Systems which has been calibrated by Deutsche Akkreditierungsstelle (DAkkS). In a second step, the luminance is then multiplied by n and divided by the voltage and current density.

Technical Effect of the Invention

The OLED device with electron transport layer 1 consisting of compound of formula 1 showed improved life time (LT97 at 30 mA/cm2 (h)) as compared to the OLED device with electron transport layer 1 consisting of comparative compound 1 with a comparable OLED performance parameters e.g. voltage and efficiency (Table 2).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims Therefore, the aforementioned embodiments should be understood to be exemplary but not limiting the present invention in any way.

TABLE 1

Properties of compound D-1 and D-2 of inventive example 1 and 2 and compound E-1

| Referred to as: | Structure | mp (° C.) | Tg (° C.) | TRO (° C.) | HOMO (eV) | LUMO (eV) | Dipole moment (Debye) |
|---|---|---|---|---|---|---|---|
| Compound D-1 | 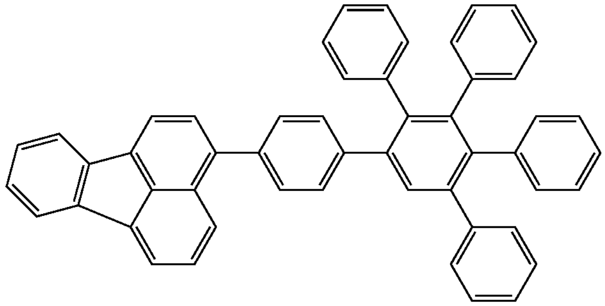 | 262 | 135 | 228 | −5.50 | −1.78 | 1.21 |
| Compound D-2 | 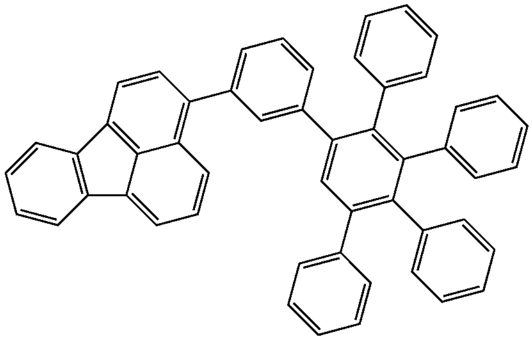 [SMILES: c1ccc(-c2cc(-c3cccc(-c4ccc5c6c(cccc46)-c4ccccc4-5)c3)c(-c3ccccc3)c(-c3ccccc3)c2-c2ccccc2)cc1] | 230 | 129 | 216 | −5.57 | −1.78 | 1.02 |
| Compound D-31 | 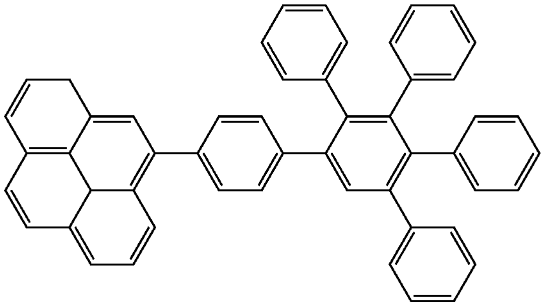 [SMILES: C1=CC2=C(c3ccc(-c4cc(-c5ccccc5)c(-c5ccccc5)c(-c5ccccc5)c4-c4ccccc4)cc3)C=C3CC=CC4=C3C2C(=C1)C=C4] | — | — | — | −4.17 | −2.16 | 1.01 |

TABLE 1-continued
Properties of compound D-1 and D-2 of inventive example 1 and 2 and compound E-1
| Referred to as: | Structure | mp (° C.) | Tg (° C.) | TRO (° C.) | HOMO (eV) | LUMO (eV) | Dipole moment (Debye) |
|---|---|---|---|---|---|---|---|
| Compound D-32 | 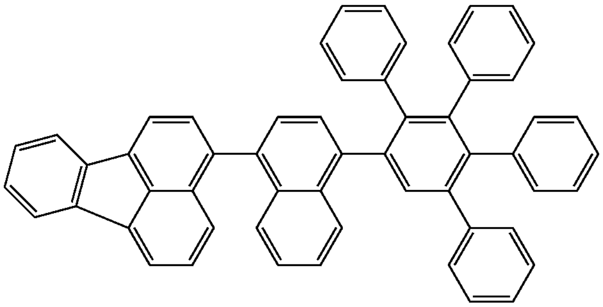 [SMILES: c1ccc(-c2cc(-c3ccc(-c4ccc5c6c(cccc46)-c4ccccc4-5)c4ccccc34)c(-c3ccccc3)c(-c3ccccc3)c2-c2ccccc2)cc1] | — | — | — | −5.42 | −1.77 | 1.03 |
| Compound D-33 | 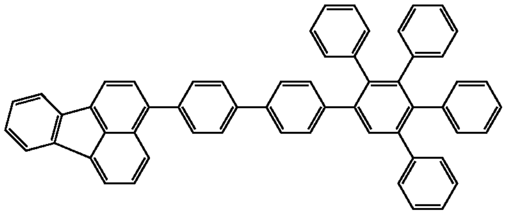 [SMILES: c1ccc(-c2cc(-c3ccc(-c4ccc(-c5ccc6c7c(cccc57)-c5ccccc5-6)cc4)cc3)c(-c3ccccc3)c(-c3ccccc3)c2-c2ccccc2)cc1] | — | — | — | −5.48 | −1.82 | 1.20 |
| Compound E-1 | 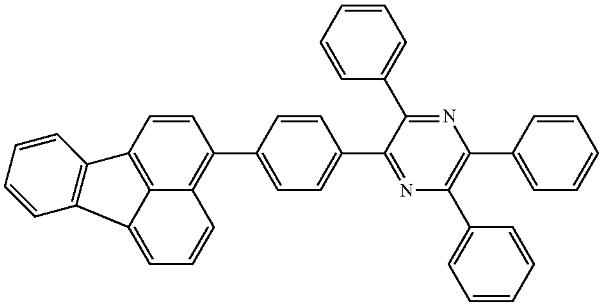 [SMILES: c1ccc(-c2nc(-c3ccccc3)c(-c3ccc(-c4ccc5c6c(cccc46)-c4ccccc4-5)cc3)nc2-c2ccccc2)cc1] | 237 | 121 | 222 | −5.54 | −1.88 | 0.58 |
| Compound E-3 | 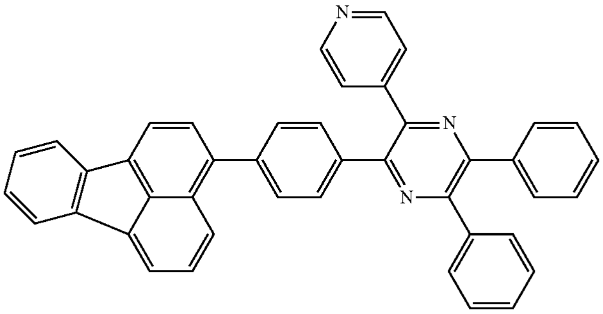 [SMILES: c1ccc(-c2nc(-c3ccncc3)c(-c3ccc(-c4ccc5c6c(cccc46)-c4ccccc4-5)cc3)nc2-c2ccccc2)cc1] | — | — | — | −5.63 | −1.96 | 3.08 |

TABLE 1

Performance of an organic electroluminescent device comprising an electron transport layer 1 comprising a compound of formula 1

| | Compound in ETL1 | Thickness ETL1 (nm) | Matrix compound | Concentration of matrix compound in ETL2 (vol-%) | Alkali organic complex | Concentration of alkali organic complex (vol.-%) | Thickness ETL2 (nm) | Operating voltage at 10 mA/ $cm^2$ (V) | cd/A efficiency at 10 mA/ $cm^2$ (cd/A) | LT97 at 30 mA/ $cm^2$ (h) |
|---|---|---|---|---|---|---|---|---|---|---|
| Comparative example 1 | 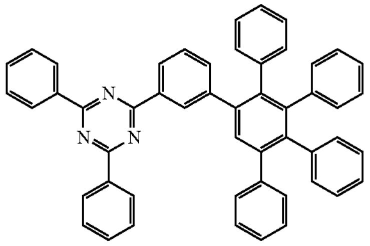 [SMILES: c1ccc(-c2nc(-c3ccccc3)nc(-c3cccc(-c4cc(-c5ccccc5)c(-c5ccccc5)c(-c5ccccc5)c4-c4ccccc4)c3)n2)cc1] CC-1 | 5 | ETM-1 | 50 | LiQ | 50 | 31 | 3.7 | 7.9 | 47 |
| Example 1 | 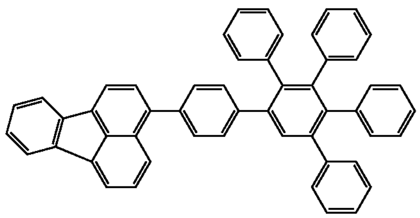 [SMILES: c1ccc(-c2cc(-c3ccc(-c4ccc5c6c(cccc46)-c4ccccc4-5)cc3)c(-c3ccccc3)c(-c3ccccc3)c2-c2ccccc2)cc1] D-1 | 5 | ETM-1 | 50 | LiQ | 50 | 31 | 3.6 | 7.0 | 80 |
| Example 2 | 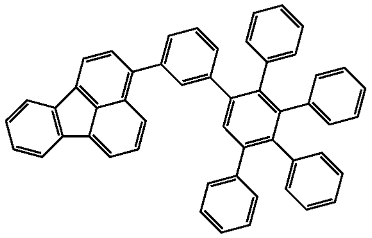 [SMILES: c1ccc(-c2cc(-c3cccc(-c4ccc5c6c(cccc46)-c4ccccc4-5)c3)c(-c3ccccc3)c(-c3ccccc3)c2-c2ccccc2)cc1] D-2 | 5 | ETM-1 | 50 | LiQ | 50 | 31 | 3.6 | 6.9 | 98 |

The features disclosed in the foregoing description and in the dependent claims may, both separately and in any combination thereof, be material for realizing the aspects of the disclosure made in the independent claims, in diverse forms thereof.

The invention claimed is:

1. Compound of Formula (I)

(I)

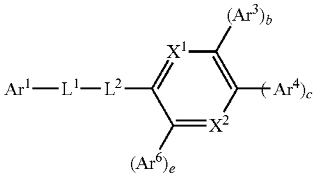

wherein $Ar^1$ is substituted or unsubstituted fluoranthenyl, wherein the one or more substituent(s), if present in $Ar^1$, are independently selected from the group consisting of $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, $PY(R)_2$, OR, SR, (C═O)R, (C═O)N(R)$_2$, Si(R)$_3$, (S═O)R, and (S═O)$_2$ R, wherein, Y is O or S, R are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

$X^1$ and $X^2$ are nitrogen, or $X^1$ is C—$(Ar^2)_a$ and $X^2$ is C—$(Ar^5)_a$;

$L^1$ may represent a single bond or is selected from the group consisting of phenylene, biphenylene, triphenylene, and naphthylene;

$L^2$ is selected from the group consisting of substituted or unsubstituted phenylene, substituted or unsubstituted biphenylene, substituted or unsubstituted triphenylene, and substituted or unsubstituted naphthylene, wherein the one or more substituent(s), if present in $L^2$, are independently selected from the group consisting of $C_6$ to $C_{18}$ aryl, $C_3$ to $C_{20}$ heteroaryl, D, F, CN, $C_1$ to $C_{16}$ alkyl, $C_1$ to $C_{16}$ alkoxy, nitrile, $PY(R)_2$ with Y being O or S, OR, SR, (C═O)R, (C═O)N(R)$_2$, Si(R)$_3$, (S═O)R, and (S═O)$_2$R, wherein, Y is O or S, R are independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_3$-$C_{20}$ heteroaryl;

$Ar^2$, $Ar^3$, $Ar^4$, $Ar^5$ and $Ar^6$ are independently selected from the following moieties C-1 to C-12—

C-1

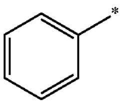

C-2

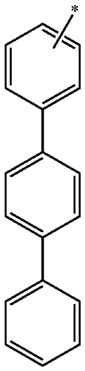

C-3

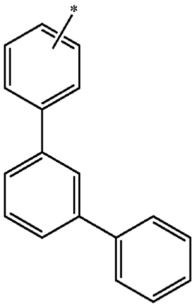

C-4

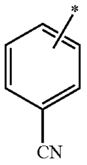

C-5

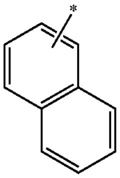

-continued

C-6

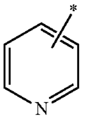

C-7

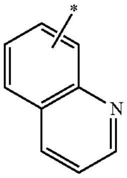

C-8

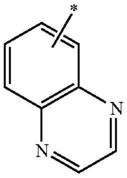

C-9

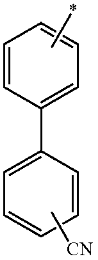

C-10

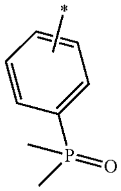

C-11

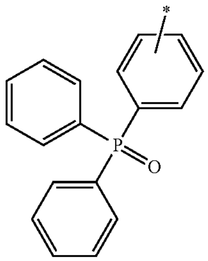

C-12

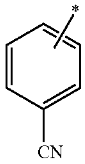

;

and a, b, c, d and e are independently selected from 0 or 1, wherein 2≤a+b+c+d+e≤5;

provided that if $X^1$ is C—$(Ar^2)_a$ and $X^2$ is C—$(Ar^5)_d$, and b and d are 1 and a+b+c+d+e=2, then $Ar^2$, $Ar^3$, $Ar^4$, $Ar^5$ and $Ar^6$ are independently selected from the group consisting of substituted or unsubstituted $C_6$ to $C_{30}$ aryl;

wherein the compound of Formula (I) has the following Formula (II)—

(II)

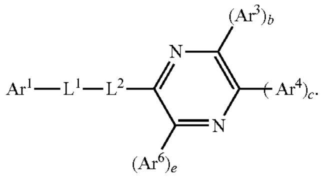

2. Compound according to claim 1, wherein 2≤a+b+c+d+e≤4.

3. Organic semiconducting layer comprising the compound of Formula (I) according to claim 1.

4. Organic semiconducting layer according to claim 3, wherein the organic semiconducting layer further comprises a metal, a metal salt or an organic metal complex.

5. Organic electronic device comprising the organic semiconducting layer according to claim 3.

6. Organic electronic device according to claim 5 further comprising an emission layer, an anode and a cathode, wherein the organic semiconducting layer is arranged between the emission layer and the cathode.

7. Organic electronic device according to claim 6 further comprising an electron transport layer, wherein the organic semiconducting layer is contacting sandwiched between the emission layer and the electron transport layer.

8. Display device comprising the organic electronic device according to claim 5.

9. Lighting device comprising the organic electronic device according to claim 5.

10. Organic electronic device according to claim 6, wherein the organic semiconducting layer is in direct contact with the emission layer.

* * * * *